United States Patent
Yamazaki et al.

(10) Patent No.: US 6,869,609 B1
(45) Date of Patent: Mar. 22, 2005

(54) METHOD FOR TREATMENT OF RENAL FAILURE AND OCCLUSIVE LESION OF BLOOD VESSELS BY ADMINISTRATION OF HEPATOCYTE GROWTH FACTOR

(75) Inventors: Naoki Yamazaki, Osaka (JP); Tomokazu Nagano, Osaka (JP); Ikue Kudo, Osaka (JP); Michitoshi Sekine, Osaka (JP)

(73) Assignee: Sumitomo Pharmaceuticals Co., Ltd., Osaka (JP)

( * ) Notice: Subject to any disclaimer, the term of this patent is extended or adjusted under 35 U.S.C. 154(b) by 0 days.

(21) Appl. No.: 09/555,629

(22) PCT Filed: Dec. 3, 1998

(86) PCT No.: PCT/JP98/05470

§ 371 (c)(1),
(2), (4) Date: Jul. 31, 2001

(87) PCT Pub. No.: WO99/27951

PCT Pub. Date: Jun. 10, 1999

(30) Foreign Application Priority Data

Dec. 3, 1997 (JP) .............................................. 9-350122

(51) Int. Cl.$^7$ ........................ A61K 38/00; A61K 38/18; C07K 14/00
(52) U.S. Cl. ........................ 424/198.1; 424/85.1; 514/2; 514/12; 530/300; 530/350; 530/399
(58) Field of Search ................................. 530/300, 350, 530/399; 424/85.1, 184.1, 198.1; 514/2, 12

(56) References Cited

U.S. PATENT DOCUMENTS

| | | | | | |
|---|---|---|---|---|---|
| 5,360,790 | A | * | 11/1994 | Humes et al. ................. | 514/12 |
| 5,654,404 | A | * | 8/1997 | Roos et al. ............... | 530/387.3 |
| 5,703,048 | A | * | 12/1997 | Roos et al. .................... | 514/12 |
| 6,133,234 | A | * | 10/2000 | Bunting et al. ................ | 514/12 |
| 6,436,388 | B2 | * | 8/2002 | Kudo et al. ................. | 424/85.1 |

FOREIGN PATENT DOCUMENTS

| EP | 0462549 A1 | * | 6/1991 |
|---|---|---|---|
| EP | 0 462 549 A1 | | 12/1991 |
| WO | WO-9712628 A1 | * | 4/1997 |
| WO | A1-9712628 | | 4/1997 |

OTHER PUBLICATIONS

Yo et al. Actions of hepatocyte growth factor as a local modulator in the kidney: potential role in pathogenesis of renal disease Kidney Int. 53(1):50–58, 1998.*
Amaike et al. Preventive effect of hepatocyte growth factor on acute side effects of cyclosporin A in mice. Cytokine 8(5): 387–394, 1996.*
Hayashi, S. Effects of LTB4 receptor anatagonist on myo-nephropathic metabolic syndrome: an experimental study. Kurume Med J 47(1): 63–72, 2000.*
Ioannou et al. Current concepts for the management of systemic lupus erythematosus in adults: a therapeutic challenge. Postgrad Med J. 78(924):599–606, 2002.*
Mizuno et al. Hepatocyte growth factor prevents renal fibrosis and dysfunction in a mouse model of chronic renal disease. J Clin Invest. 101(9):1827–1834, 1998.*
Singri et al. Acute renal failure. J Am Med Assoc 289(6): 747–751, 2003.*
Tsuji et al. Involvement of calpain in myonephropathic metabolic syndrome (MNMS). Eur J Vasc Surg. 8(4):482–488, 1994.*
Yaekashiwa et al. Simultaneous or delayed administration of hepatocyte growth factor equally represses the fibrotic changes in i murine lung injury induced by bleomycin. A morphologic study. Am J Respir Crit Care Med. 156: 1937–1944, 1997.*
Yamasaki et al. Hepatocyte growth factor protects functional and histological disorders of HgCl(2)–induced acute renal failure mice. Nephron. 90(2):195–205, 2002.*
Matsumoto et al. Jikken Igaku 15(9): 1040–1047, 1997.*
Tsukasa Igawa et al., Am. J. Physiol, vol. 265, No. 1, Pt.2, F61–F69 (1993).
Kouichi Kawaida et al., Proc. Natl. Acad. Sci. USA, vol. 91, pp. 4357–4361 (1994).
Sang Kil Ha–Kawa et al.; Jpn. Pharmacol. Ther.; 24:149–152; 1996.

* cited by examiner

Primary Examiner—Elizabeth C. Kemmerer
Assistant Examiner—Bridget E. Bunner
(74) Attorney, Agent, or Firm—Birch, Stewart, Kolasch & Birch, LLP

(57) ABSTRACT

The invention presents a preparation for continuous intravenous administration containing hepatocyte growth factor (HGF) as an active ingredient. The preparation for continuous administration of the invention is effective at a lower dose as compared with single or frequent bolus administration of HGF, and therefore side effects can be reduced.

1 Claim, 7 Drawing Sheets

Mean±SD (n=10, $:n=7), *: P<0.05  **: P<0.01 by nonparametric test

Mean±SD (n=8), **: P<0.01 by Dunnett's test

Mean±SD, *: P<0.05, **: P<0.01 by nonparametric test

METHOD FOR TREATMENT OF RENAL FAILURE AND OCCLUSIVE LESION OF BLOOD VESSELS BY ADMINISTRATION OF HEPATOCYTE GROWTH FACTOR

This application is the national phase under 35 U.S.C. § 371 of PCT International Application No. PCT/JP98/05470 which has an International filing date of Dec. 3, 1998, which designated the United States of America.

TECHNICAL FIELD

The present invention relates to a pharmaceutical preparation for continuous intravenous administration containing hepatocyte growth factor as an active ingredient.

PRIOR ART

Hepatocyte growth factor (HGF) is discovered as a potent proliferation promoting factor for mature hepatocytes, and is a protein whose gene has been cloned by gene cloning (Biochm Biophys Res Commun, 122, 1450, 1984; Proc. Natl. Acad. Sci, USA, 83, 6489, 1986; FEBS Letter, 224, 311, 1987; Nature 342, 440, 1989; Proc. Natl. Acad. Sci, USA, 87, 3200, 1990). Later studies disclosed that HGF, in vivo, not only works to repair and regenerate damaged liver as liver regenerating factor, but also has various pharmacological actions, and it is expected to be developed as medicine for kidney diseases, cerebral and neural injuries, cartilage injuries, arterial diseases, fibroid lung and others, aside from liver diseases. For example, as for the pharmacological action of HGF on renal diseases, more specifically, HGF is known to play a key role in regeneration of kidneys. In rats with one kidney removed, an expression of HGF mRNA was induced in the remaining kidney, and HGF activity was elevated (J. Biol. chem., 266, 22781, 1991). In kidneys of renal ischemic rats, HGF mRNA was induced and HGF activity was elevated (American Journal of Physiology, 265, 61, 1993), and in kidneys of mice injured by a nephrotoxin, similarly, induction of expression of HGF mRNA and elevation of HGF activity were reported (Nephron 73, 735, 1996). Therefore HGF is believed to express and function as a repair factor in renal injuries.

On the basis of such function of HGF, HGF was administered in renal injury models, and effects of HGF were reported. That is, since the above-mentioned renal ischemic models and renal injury models by nephrotoxins such as mercury (II) chloride ($HgCl_2$) and cisplatin present acute tubulorrhexis which is a pathology of acute renal failure, they have been traditionally used as disease models of acute renal failure. As a result of administration of HGF in such renal ischemic models and renal injury models, elevation of parameters of renal function disorders such as blood urea nitrogen (BUN) and blood creatinine was promptly suppressed in both injury models, and it was unveiled that HGF has a repair action on renal injuries (American Journal of Physiology, 266, 129, 1994; Proc. Natl. Acad. Sci, USA, 91, 4357, 1994).

In addition to these acute renal failure models such as renal ischemic models and renal injury models, in spontaneous nephrotic models regarded as chronic renal failure models, HGF is also found to present marked effects (Japan Disease Model Academy Record Vol. 13, 113, Lecture 28, 1997).

Thus, as a result of evaluation of effects of HGF in various animal models, the efficacy of HGF in renal diseases ranging from acute renal failure to chronic renal failure has been elucidated. However, the best administration route and dose of HGF has not been known.

Generally, it is common knowledge that a protein preparation is intravenously administered. Concerning intravenous administration of HGF to renal disease models, for example, frequent intravenous administrations (CYTOKINE, 8, 387, 1996; Proc. Natl. Acad. Sci, USA, 91, 4357, 1994) and single intravenous administrations (J. American Society of Nephrology, 1835, Lecture A2944, 1996; J. of Japan Society of Nephrology, Vol. 39, 260, Lecture 0-302) are reported. However, continuous intravenous administration of HGF in renal disease models has not been reported yet.

The present inventors intensively studied the dose and route of administration for applying HGF to renal disease. As method of administration of HGF for renal disease, intravenous bolus administration and continuous intravenous administration were investigated, and the intravenous bolus administration is established in evaluation, whereas the continuous intravenous administration is not established in evaluation, because 1) the cannula is often pulled out during continuous administration, 2) it takes much time in operation in the case of cannulation into the cervical vein although the cannula is less likely to be pulled out, and 3) pathological control is difficult to due stress to animals, among other problems. In such background, so far, attempts of continuous intravenous administration in renal disease models have not been reported, and hence it is not known whether the continuous intravenous administration of HGF is effective or not.

In such circumstances, the inventors have succeeded in establishment of evaluation system of continuous intravenous administration in mercury chloride model mice by making some improvements, including indwell ing of wing-shaped needle in tail vein instead of cervical vein, and anesthesia of mice. Using this model, effects of continuous intravenous administration of HGF were studied actually, and notable effects of HGF by continuous administration, that is, effects of continuous intravenous administration of HGF on renal disease have been disclosed for the first time.

The inventors further compared the effects between intravenous bolus administration and continuous intravenous administration, and discovered, surprisingly enough, that the dose can be substantially reduced in continuous administration as compared with bolus administration. Since the dose is decreased as compared with the conventional bolus administration, it means that side effects are decreased in clinical use.

On the basis of these findings, the inventors have further promoted researches, and found that the continuous intravenous administration of HGF is more effective than bolus administration on occlusive lesion of blood vessels. More specifically, in the glycerol model for administering glycerol in muscles, it is accompanied by injury of skeletal muscles, a large quantity of myoglobin is released from skeletal tissues into blood, and various components such as creatine kinase, creatine, potassium, phosphoric acid and purine precursor are released into the blood. Thus, the glycerol model is regarded as the so-called MNMS (myonephropathic-metabolic syndrome) model such as rhabdomyolysis, myoglobinuria and detrition syndrome that are accompanied by decay of skeletal tissues (Syndrome by Clinical Regions of Japan, Supplement 17, Nephrotic Syndrome, pp. 523–526, 1997, etc.).

On the other hand, in occlusive lesion of blood vessels, if ischemia continues due to acute vascular occlusion, ischemic muscular necrosis widely occurs, and MNMS that elevates levels of creatine kinase, potassium and myoglobin in serum is induced. Therefore, the glycerol model is regarded also as a model of occlusive lesion of blood vessel. In such glycerol model, too, the continuous intravenous administration of HGF is more effective than the bolus administration, and the continuous intravenous administration of HGF has been proved to be effective also on occlusive lesion of blood vessel.

As a result of further studies, the inventors have found that the continuous intravenous administration of HGF is more effective than the bolus administration in platelet increasing action of HGF, and generally that the continuous intravenous administration is more effective than single or frequent intravenous bolus administration of HGF, and hence concluded that the effect can be expressed at low dose.

The invention is devised on the basis of these findings, and it is hence an object of the invention- to present a pharmaceutical preparation for continuous intravenous administration containing HGF as an active ingredient.

DISCLOSURE OF THE INVENTION

The invention presents a pharmaceutical preparation for continuous intravenous administration containing HGF as an active ingredient. More particularly, it presents a pharmaceutical preparation for continuous intravenous administration effective for treatment and prevent ion of renal diseases, occlusive lesion of blood vessels, and others. The pharmaceutical preparation for continuous intravenous administration of the invention is lower in dose as compared with the intravenous bolus administration, and is hence effective to decrease side effects.

BEST MODE FOR CARRYING OUT THE INVENTION

Figure 1:
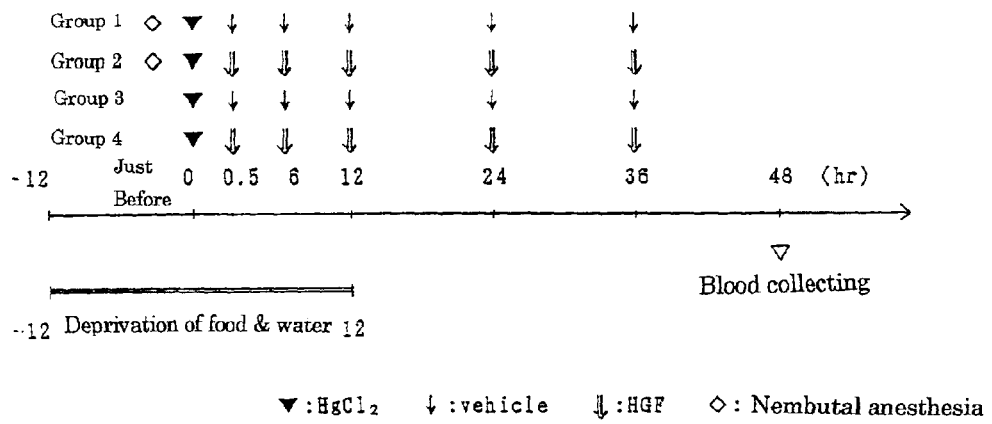
FIG. 1 is a diagram showing an outline of administration schedule of Example 1-3).

HGF used in the invention is a known substance, compounds prepared by various methods can be used if they are purified to an extent that they may be used as a medicine, or any commercial product can be used (for example, Toyobo Code No. HGF-101). To prepare HGF, for example, primary culture cells or a cell line which produce(s) HGF are cultivated, and HGF is obtained by isolating from the culture supernatant and purifying. Or by gene engineering technique, a gene encoding HGF is inserted into a proper vector, and it is incorporated into a proper host to transform, and a desired recombinant HGF is obtained from the culture supernatant of this transformant (for example, Nature, 342, 440, 1989; Japanese Laid-open Patent No. 5-111383; Biochem. Biophys. Res. Commun. 163, 967, 1989). The host cell is not particularly limited, and various host cells conventionally used in gene engineering technique may be used, which are, for example. *Escherichia coli*, yeast, and animal cells. Thus obtained HGF is not limited as far as it has substantially the same action as the natural HGF, and for example, one or plural amino acids in the amino acid sequence may be replaced, deleted and/or added, or similarly sugar chain may be replaced, deleted and/or added.

The preparation for continuous intravenous administration of the invention may be applied in various diseases in which the medicinal effects of HGF have been recognized, and in particular it is preferably used in renal diseases and occlusive lesion of blood vessels. The renal diseases mentioned above include both chronic renal diseases (nephropathy, renal failure, nephritis) and acute renal diseases. Specific examples include acute renal failure, chronic renal failure, glomerulonephritis, nephrotic syndrome, systemic lupus erythematosus, glomerular diseases accompanying hepatic disease, diabetic nephropathy, tubulointerstitial nephritis, renal vascular disorder, hypertensive renal disorder, nephro-urinary calculus, urinary tract infection, occlusive nephropathy, cystic renal disease, nephro-urinary tumor, hereditary renal disease, kidney transplant, complication by kidney transplant, and drug-induced renal disorder. Examples of occlusive lesion are lower limb ischemia, acute arterial occlusion, chronic arterial occlusion, arteriosclerosis obliterans, arterial embolism, arterial thrombosis, Buerger's disease, venous occlusion, venous thrombosis, thrombotic phlebitis, angiodysplasia, vascular damage, coronary occlusion, coronary stenosis, pulmonary embolism, and arterial occlusion of organs (Clinical Angiology, Bunkodo, 1992; Therapeutics, Vol. 31, No. 3, pp. 284–338, 1997).

At this time, the active ingredient of HGF may be combined with additives as required, such as pH regulating agent, buffer, stabilizer, preservative, or solubilizer. The dose varies with the symptom, age, sex and others, and, for example, in the case of treatment or prevention of renal disease, a dose of 500 μg/head/hr or less, preferably 60 μg/head/hr or less is intravenously injected in 30 minutes to 5 hours, preferably 30 minutes to 3 hours. For treatment or prevention of occlusive lesion of blood vessel, a dose of 1800 μg/head/hr or less, preferably 200 μg/head/hr or less is intravenously injected in 30 minutes to 3 hours, preferably 30 minutes to 1.5 hours.

If the effect is not enough by single continuous administration, the continuous administration may be repeated plural times.

The timing of administration of the preparation for continuous intravenous administration of the invention is not particularly specified, but as described in the following Examples, in acute renal failure, notable effects are exhibited by continuous administration in initial phase of onset, and it is preferred to administer in initial phase of disease of the patient.

The preparation for continuous intravenous administration of the invention is used for the purpose of prevention, aside from the therapeutic purpose as mentioned above. For example, acute renal failure due to ischemic or nephrotoxic cause is the disease taking place as side effect of surgical bleeding or administration of antibiotics, anti-tumor agent or contrast medium, and therefore onset of such acute renal failure may be predicted depending on the degree of bleeding, dose of antibiotic or contrast medium, or condition of patient. In such a case, the preparation for continuous intravenous administration of the invention may be used for preventive purpose of acute renal failure.

INDUSTRIAL APPLICABILITY

The invention presents the preparation for continuous intravenous administration containing HGF as an active ingredient. The preparation for continuous administration of the invention can reduce dose as compared with bolus administration, and therefore side effects are decreased.

EXAMPLES

Preferred Examples of the invention are described below, but it must be noted that the invention is not limited to the illustrated Examples alone.

Example 1
Study on Continuous Intravenous Administration of HGF in Mouse Renal Disease Model (1)
1) Animals Male BALB/c mice (5 or 6 weeks old) were purchased from SLC, and preliminarily raised in the conditions of temperature of 23±2° C., humidity of 55±10%, lighting from 8:00 to 20:00, and free access to diet and water, and used for experiment at the age of 6.5 weeks to 8 weeks.

2) Intravenous Continuous Administration to Mice

A 1 ml syringe (Terumo Corp.) was preliminarily filled with HGF or vehicle, and a winged needle (Terumo) was attached to it with a three-way stopcock (Terumo) placed between them (then the wing being cut off). Mice were anesthetized by Nembutal (100 mg/kg, s.c.). The needle was inserted into the tail vein and kept on a hot plate at 37° C. and fixed with tape. A breathing hole was opened in the bottom of a conical tube having a proper size for BALB/c mouse, and also a slit for projecting the tail was opened at the opposite side of the tube, and then each mouse was put in the tube. The syringes were set in an infusion pump (Neuro Science Corp.), and piston positions were aligned by the three-way stopcock, and the evaluation system for continuous intravenous administration was set up, and used in the following experiments (Examples 1 to 3).

3) Study on Effects of Anesthesia

Since Nembutal is used for anesthesia in this evaluation system as described in 2), influence of anesthesia on model preparation and effect of HGF were investigated in the first place. An outline of administration schedule is shown in FIG. 1.

Male BALB/c mice at the age of 8 weeks were divided into four groups of 8 animals each, and 8.5 mg/kg of $HgCl_2$ was subcutaneously administered in the back in all mice. This time was hour 0. Neither diet nor water was given from 12 hours before to 12 hours after $HgCl_2$ injection. In group 1 and group 2, before administration of $HgCl_2$, 100 mg/kg of Nembutal was subcutaneously administered in the rear back. At 0.5, 6, 12, 24, and 36 hours after administration of $HgCl_2$, vehicle was administered in group 1 and group 3, and HGF in group 2 and group 4. The dose of HGF was 500 μg/kg/shot. Blood was sampled from all mice 48 hours after $HgCl_2$ injection, and the serum was separated, and the blood urea nitrogen (BUN) and creatinine were measured (using Synchron CX3 System Delta by Beckmann). Human recombinant HGF (same in the following experiments) was used, and the vehicle was 10 mM citric acid buffer (pH 6.0) containing 0.01% Tween 80 and 0.3 M NaCl. Statistical analysis was by Tukey's test.

Figure 2:
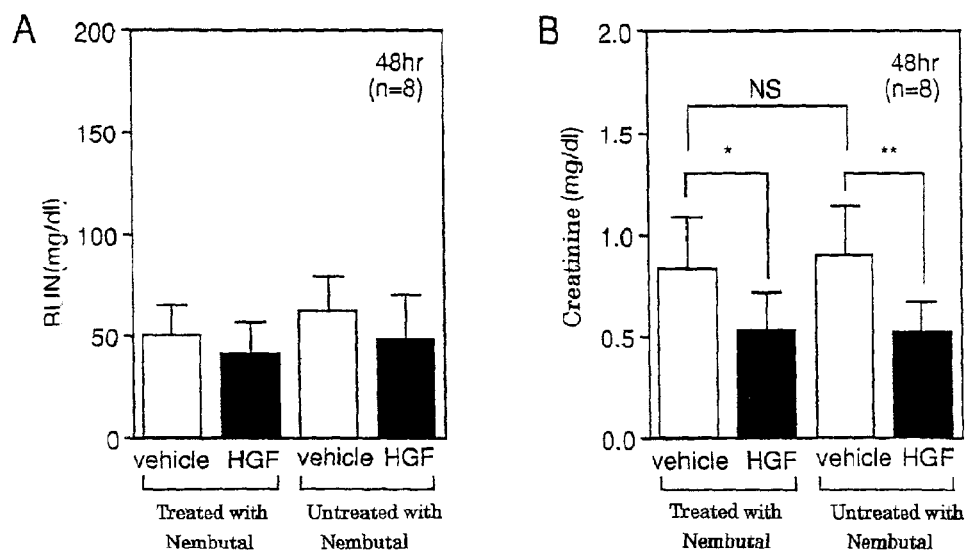
FIG. 2 is a graph showing an influence of anesthesia on the present evaluation system, in which A represents the influence on BUN, and B represents the influence on creatinine.

Results are shown in FIG. 2. A degree of creatinine elevation was not different notably regardless of anesthesia. By HGF, a significant suppression of creatinine was observed, but a degree of effect was hardly influenced by anesthesia. It was hence known that influence of anesthesia could be practically ignored when evaluating the effect of HGF.

4) Evaluation of Effect by Continuous Intravenous Administration

Figure 3:
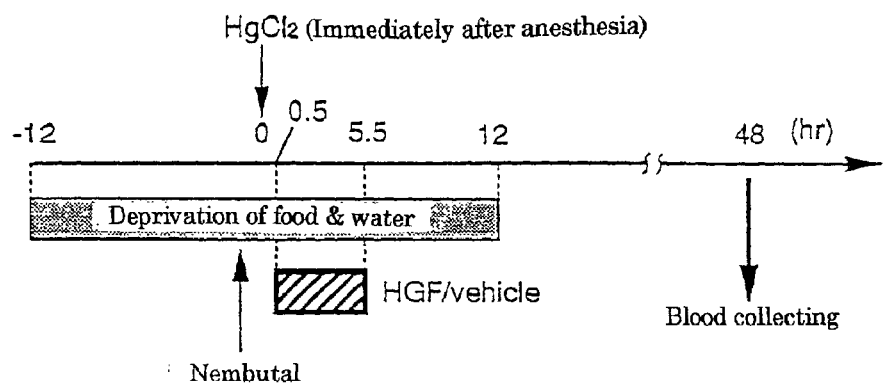
FIG. 3 is a diagram showing an outline of administration schedule of Example 1-4).

An outline of administration schedule is shown in FIG. 3.

Male BALB/c mice at the age of 8 weeks were divided into two groups of 10 animals each, and 8.5 mg/kg of $HgCl_2$ was subcutaneously administered in the back in all mice. This time was hour 0. Neither diet nor water was given from 12 hours before to 12 hours after $HgCl_2$ injection. Continuous intravenous administration of vehicle (group 1) or HGF (group 2) was performed by using the evaluation system mentioned in 2). Just before administration of $HgCl_2$, mice were anesthetized with Nembutal (100 mg/kg, s.c.), and from 0.5 hr after $HgCl_2$ injection, the administration was started. HGF (1000 μg/kg/day) was administered continuously for 5 hours at 200 μg/kg/hr. Blood was sampled from all mice 48 hours after $HgCl_2$ injection, and the serum was separated, and the blood urea nitrogen (BUN) and creatinine were measured (using Synchron CX3 System Delta by Beckmann). Statistical analysis was by t-test.

Figure 4:
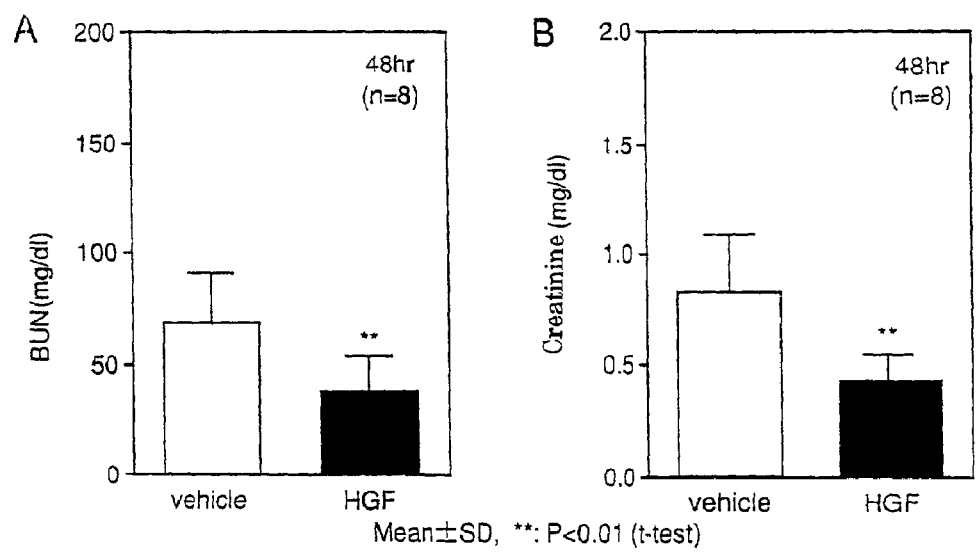
FIG. 4 is a graph showing effects of continuous intravenous administration of HGF 200 μg/kg/hr (1000 μg/kg/day) from 0.5 hr after to 5.5 hr after administration of $HgCl_2$, in which A represents the effect on BUN, and B represents the effect on creatinine.

Results are shown in FIG. 4. Both BUN and creatinine were significantly suppressed by continuous intravenous administration of HGF. Therefore, it was clarified that continuous intravenous administration of HGF is effective for renal disease.

Example 2
Study on Continuous Intravenous Administration of HGF in Mouse Renal Disease Model (2)
1) Animals Male BALB/c mice (6 weeks old) were purchased from SLC, and preliminarily raised in the conditions of temperature of 23±2° C., humidity of 55±10%, lighting from 8:00 to 20:00, and free access to diet and water, and used for experiment at the age of 6.5 weeks.

2) Attempt to Reduce the Dose of HGF (1)

Figure 5:
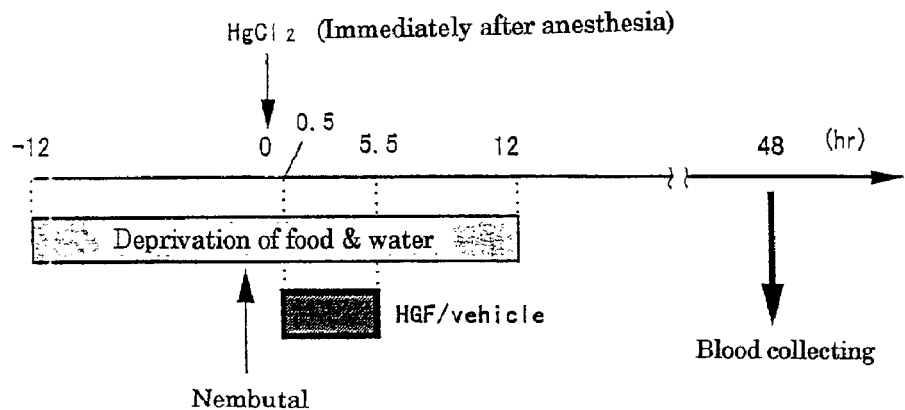
FIG. 5 is a diagram showing an outline of administration schedule of Example 2-2).

Since the efficacy was confirmed in Example 1-4) by administering HGF for 5 hours at a rate of 200 μg/kg/hr, the rate of administration of HGF was reduced from 200 μg/kg/hr to 60 μg/kg/hr. An outline of administration schedule is shown in FIG. 5.

Male BALB/c mice (6.5 weeks) were divided into three groups of 10 animals each, and anesthetized by Nembutal (100 mg/kg, s.c.). Immediately after Nembutal injection 8.5 mg/kg of $HgCl_2$ was subcutaneously administered in the back in all mice. This time was hour 0. Neither diet nor water was given from 12 hours before to 12 hours after $HgCl_2$ injection. Vehicle was administered in group 1. HGF in group 2 at 60 μg/kg/hr (300 μg/kg/day), and HGF in group 3 at 200 μg/kg/hr (1000 μg/kg/day), by continuous intravenous injection from 0.5 to 5.5 hours after $HgCl_2$ injection. Blood was sampled from all mice 48 hours after $HgCl_2$ injection, and the serum was separated, and the blood urea nitrogen (BUN) and creatinine were measured (using Synchron CX3 System Delta by Beckmann). The data was statistically processed by nonparametric test because equal variance was denied in the Bartlett's test.

Figure 6:
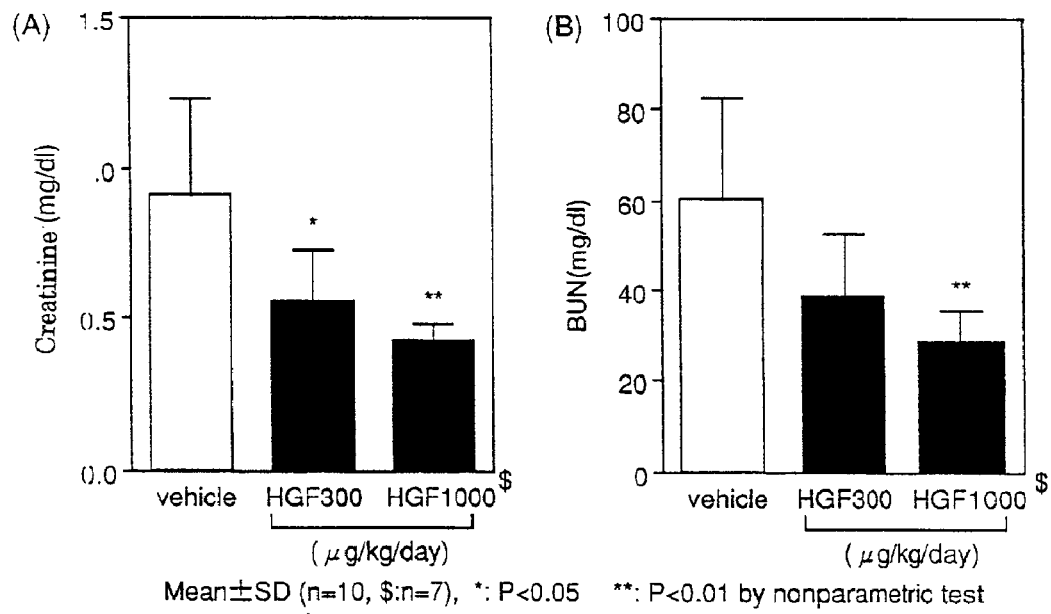
FIG. 6 is a graph showing effects of continuous intravenous administration of HGF 60 μg/kg/hr (300 μg/kg/day) and HGF 200 μg/kg/hr (1000 μg/kg/day) from 0.5 hr after to 5.5 hr after administration of $HgCl_2$, in which A represents the effect on creatinine, and B represents the effect on BUN.

Results are shown in FIG. 6. Although the efficacy was slightly inferior to that of the positive control of 200 μg/kg/hr (1000 μg/kg/day), the creatinine elevation was significantly suppressed at 60 μg/kg/hr (300 μg/kg/day). A suppressing tendency was noted in BUN if not significant.

3) Attempt to Reduce the Dose of HGF (2)

Figure 7:
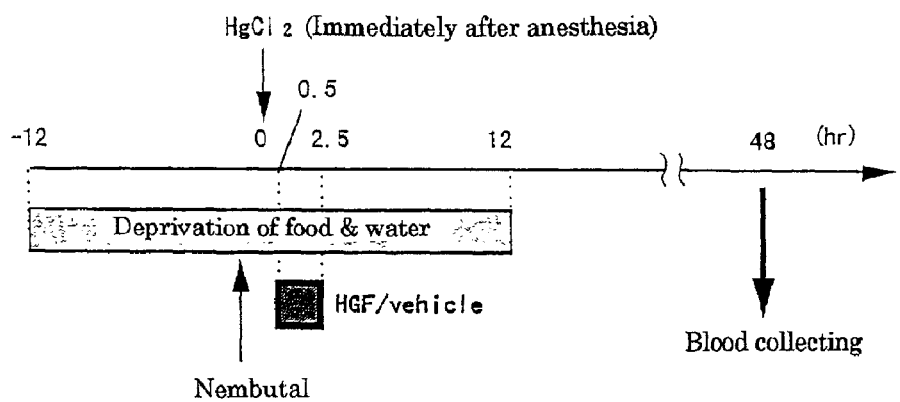
FIG. 7 is a diagram showing an outline of administration schedule of Example 2-3).

The time of continuous administration mentioned in 2) was reduced from 5 hours to 2 hours. An outline of administration schedule is shown in FIG. 7.

Male BALB/c mice (6.5 weeks) were divided into three groups of 10 animals each, and anesthetized by Nembutal (100 mg/kg, s.c.). Immediately after Nembutal injection 8.5 mg/kg of $HgCl_2$ was subcutaneously administered in the back in all mice. This-time was hour 0. Neither diet nor water was given from 12 hours before to 12 hours after $HgCl_2$ injection. Vehicle was administered in group 1, HGF in group 2 at 60 μg/kg/hr (120 μg/kg/day), and HGF in group 3 at 200 μg/kg/hr (400 μg/kg/day), by continuous intravenous injection from 0.5 to 2.5 hours after $HgCl_2$ injection. Blood was sampled from all mice 48 hours after $HgCl_2$ injection, and the serum was separated, and the blood urea nitrogen (BUN) and creatinine were measured (using Synchron CX3 System Delta by Beckmann). The data was statistically processed by nonparametric test because equal variance was denied in the Bartlett's test.

Figure 8:
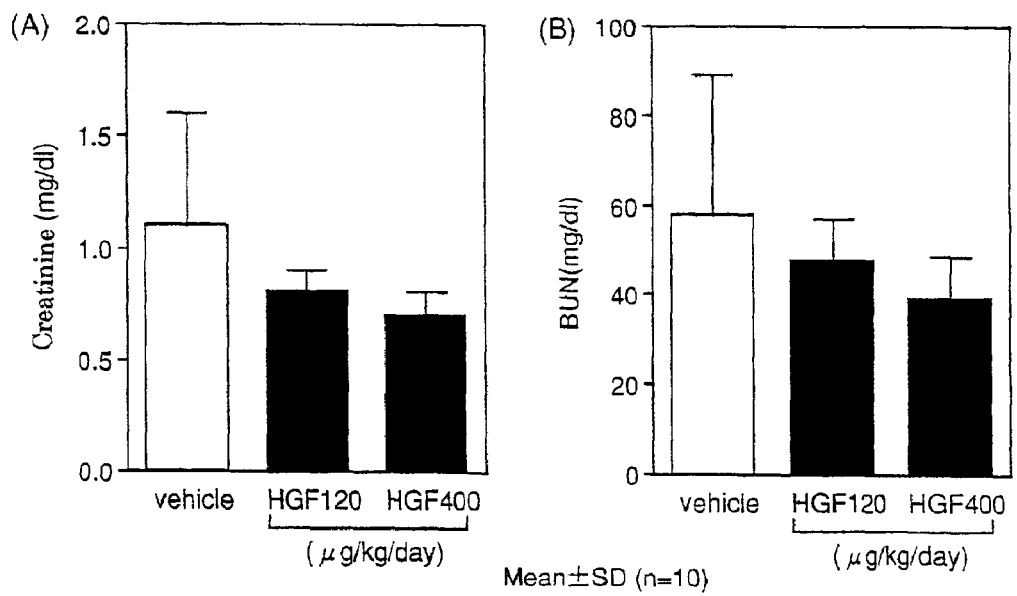
FIG. 8 is a graph showing effects of continuous intravenous administration of HGF 60 μg/kg/hr (120 μg/kg/day) and HGF 200 μg/kg/hr (400 μg/kg/day) from 0.5 hr after to 2.5 hr after administration of $HgCl_2$, in which A represents the effect on creatinine, and B represents the effect on BUN.

Results are shown in FIG. 8. In this experiment, the BUN and creatinine were not improved significantly, but an improving tendency was noted.

4) Dose-Dependent Effect by Intravenous Bolus Administration of HGF

Figure 9:
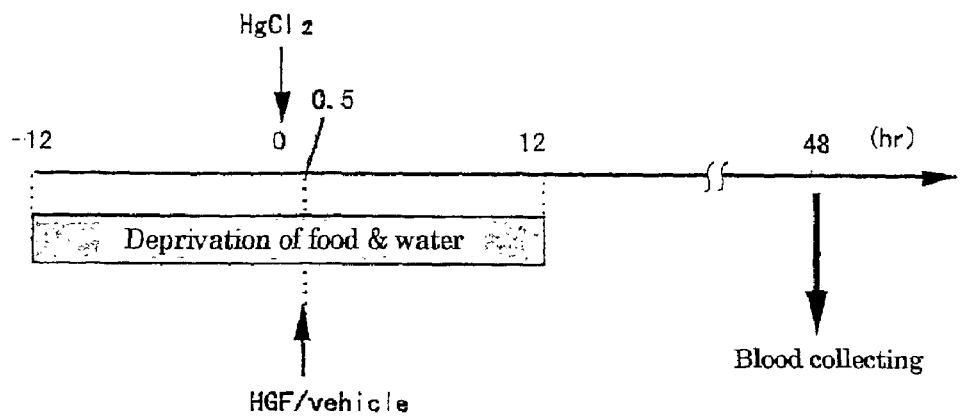
FIG. 9 is a diagram showing an outline of administration schedule of Example 2-4).

By way of comparison with continuous intravenous administration, the dose-dependent effect by intravenous bolus administration of HGF was investigated. An outline of administration schedule is shown in FIG. 9.

Male BALB/c mice were divided into five groups of 10 animals each, and 8.5 mg/kg of $HgCl_2$ was subcutaneously administered in the back in all mice. This time was hour 0. Neither diet nor water was given from 12 hours before to 12 hours after $HgCl_2$ injection. In group 1, vehicle was administered in the tail vein 0.5 hour after $HgCl_2$ injection. In groups 2 to 5, HGF (100, 300, 1000, 3000 μg/kg, respectively) was administered in the tail vein 0.5 hour after $HgCl_2$ injection. Blood was sampled from all mice 48 hours after $HgCl_2$ injection, and the serum was separated, and the blood urea nitrogen (BUN) and creatinine were measured (using Synchron CX3 System Delta by Beckmann). The data was statistically processed by Dunnett's test.

Figure 10:
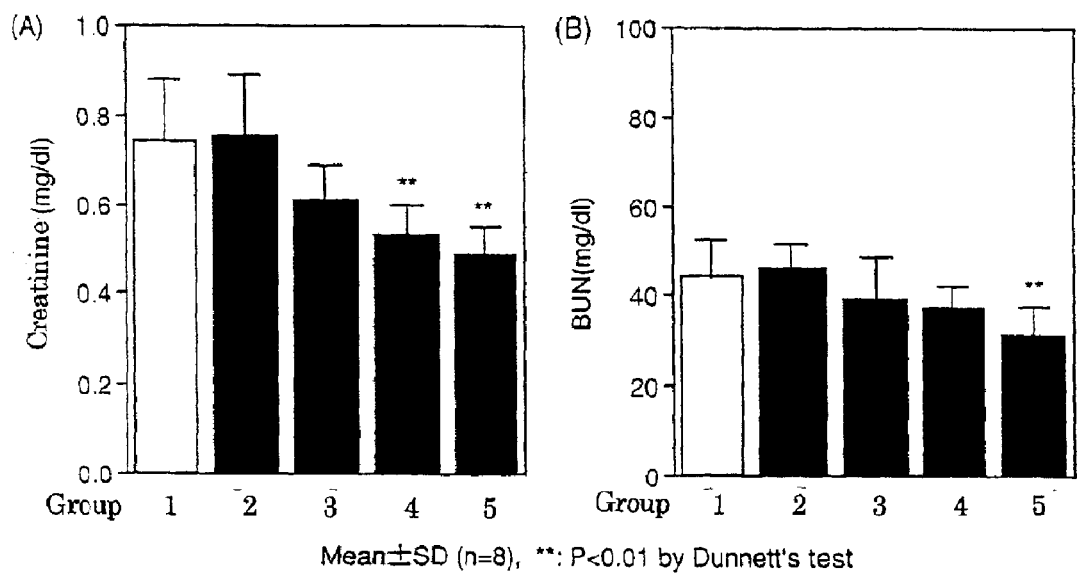
FIG. 10 is a graph showing effects of intravenous bolus administration of HGF (100 μg/kg (group 2), 300 μg/kg (group 3), 1000 μg/kg (group 4), and 3000 μg/kg (group 5)) at 0.5 hr after administration of $HgCl_2$, in which A represents the effect on creatinine, and B represents the effect on BUN.

Results are shown in FIG. 10. The creatinine: level was significantly improved at dose of 1000 μg/kg/day or more, but only an improving tendency was noted at 300 μg/kg/day, and no effect was observed at 100 μg/kg/day. By contrast, by continuous intravenous administration, a significant improvement was recognized at 300 μg/kg/day (see 2 above), and an improving tendency was noted at 120 μg/kg/day (see 3 above). As a result, as compared with the single intravenous administration, it was found that the dose could be saved in the continuous intravenous administration. The inventors have also compared the effect between frequent intravenous administration and single shot by adjusting the total dose, and reported that similar results are obtained in single shot and frequent administration (J. of Japan Society of Nephrology. Vol. 39, 260. Lecture 0-302). Therefore, the continuous intravenous administration of HGF can decrease the dose as compared with single shot or frequent intravenous bolus administration.

Example 3

Study on Continuous Intravenous Administration of HGF in Mouse Renal Disease Model (3)

1) Animals

Male BALB/c mice were purchased at the age of 6 weeks from SLC, and preliminarily raised in the conditions of temperature of 23±2° C., humidity of 55±10%, lighting from 8:00 to 20:00, and free access to diet and water, and used for experiment.

2) Attempt to Reduce the Dose of HGF

Figure 11:
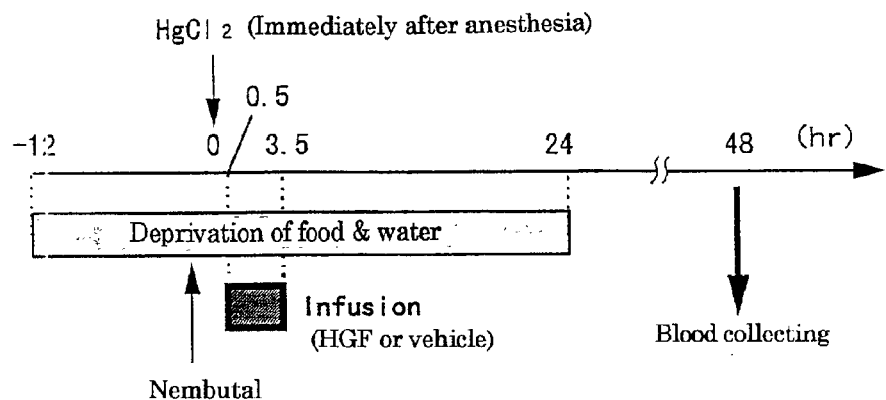
FIG. 11 is a diagram showing an outline of administration schedule of Example 3-2).

In Example 2-2), although the dose was reduced to 300 μg/kg/day, but at 120 μg/kg/day, only an improving tendency was noted, and significant improvement was not obtained. It was hence attempted to study at an approximately intermediate dose of 180 μg/kg/day. An outline of administration schedule is shown in FIG. 11.

Male BALB/c mice (6.5 weeks) were divided into three groups of 10 animals each, and anesthetized by Nembutal (100 mg/kg, s.c.). Immediately after Nembutal injection 9 mg/kg of $HgCl_2$ was subcutaneously administered in the back in all mice. This time was hour 0. Neither diet nor water was given from 12 hours before to 12 hours after $HgCl_2$ injection. Vehicle was administered in group 1, HGF in group 2 at 60 μg/kg/hr (180 μg/kg/day), and HGF in group 3 (positive control) at 200 μg/kg/hr (600 μg/kg/day), by continuous intravenous injection from 0.5 to 3.5 hours after $HgCl_2$ injection. Blood was sampled from all mice 48 hours after $HgCl_2$ injection, and the serum was separated, and creatinine and blood urea nitrogen (BUN) were measured (using Synchron CX3 System Delta by Beckmann). The data was statistically processed by nonparametric test because equal variance was denied in the Bartlett's test.

Figure 12:
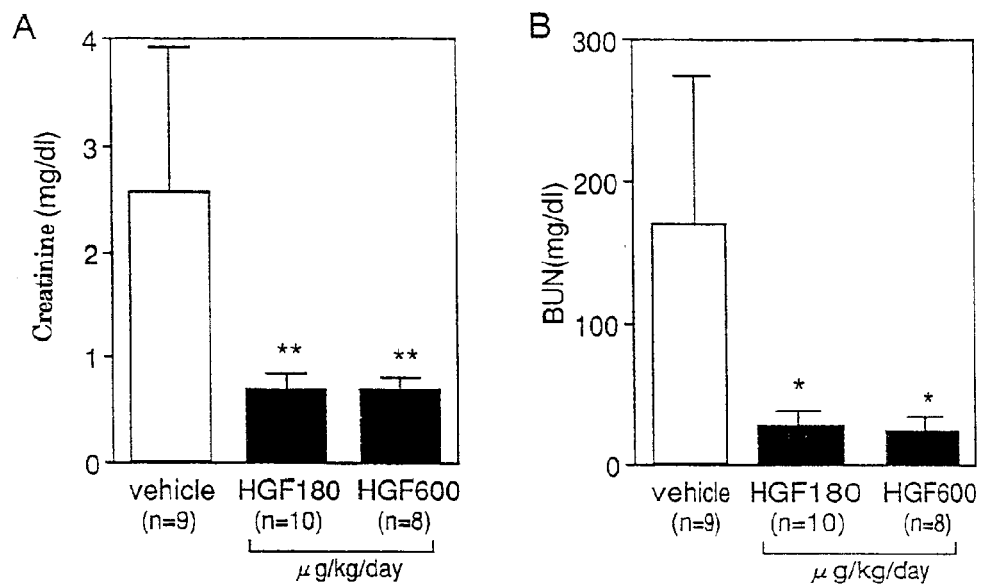
FIG. 12 is a graph showing effects of continuous intravenous administration of HGF 60 μg/kg/hr (180 μg/kg/day) and HGF 200 μg/kg/hr (600 μg/kg/day) from 0.5 hr after to 3.5 hr after administration of $HgCl_2$, in which A represents the effect on creatinine, and B represents the effect on BUN.

Results are shown in FIG. 12. In HGF 180 μg/kg/day group, elevation of creatinine and BUN was significantly suppressed as compared with vehicle group. Its suppression was nearly same as positive control (HGF 600 μg/kg/day group).

Example 4

Study on Continuous Intravenous Administration of HGF in Rat Glycerol Model

1) Materials and Method

Male Wistar rats at the age of 7 to 8 weeks (weighing about 200 g) were used. Water was withheld form 15 hours before to 8 hours after glycerol injection. 50% glycerol was intramuscularly administered (10 ml/kg) under ether anesthesia. An intravenous continuous infusion of HGF (1 mg/kg, 30 minutes) or bolus administration of HGF (3 times, total 750 μg/kg) was started 8 hours after glycerol injection. The survival of the rats was observed for 11 days after the administration of glycerol.

2) Results

Survival rate on 11th day after glycerol administration was 2/8 in control group and 8/10 in HGF group by continuous administration. By chi-square test, HGF significantly elevated the survival rate ($P<0.05$). In the case of bolus administration, the survival rate was 5/8 in control group and 5/8 in HGF group, and the life-saving effect by HGF was not recognized. It was therefore found that continuous administration tends to be more beneficial than bolus administration.

Thus, in rat glycerol models, it is revealed that continuous intravenous administration of HGF is more effective than bolus administration. Therefore, in occlusive lesion of blood vessels expressing MNMS that is similar to glycerol models, it is found that continuous intravenous administration of HGF is more effective than intravenous bolus administration.

Example 5

Study on Continuous Intravenous Administration of HGF for Increase of Platelet Counts 1) Materials and Method Male Fisher rats of 7 to 8 weeks of age were used. In continuous administration, HGF was diluted to 2 ml/kg/2 hr with vehicle of PPS containing 0.01% of Tween 80 and 0.25% of HAS, and administered in tail vein. A single dose was 0.25 mg/kg, and only vehicle was administered in control group. The administrations were carried out for 7 consecutive days at the rate of twice a day, blood was sampled next day after the final administration, and platelets were counted by using a semiautomatic blood cell count analyzer (Sysmex F-800).

In bolus administration, HGF was diluted to 1 ml/kg/shot with vehicle, and administered in caudal vein. Single doses were 0, 0.125, 0.25, 0.5, 1, and 2 mg/kg, which were administered for 7 consecutive days at the rate of twice a day.

2) Results

Figure 13:
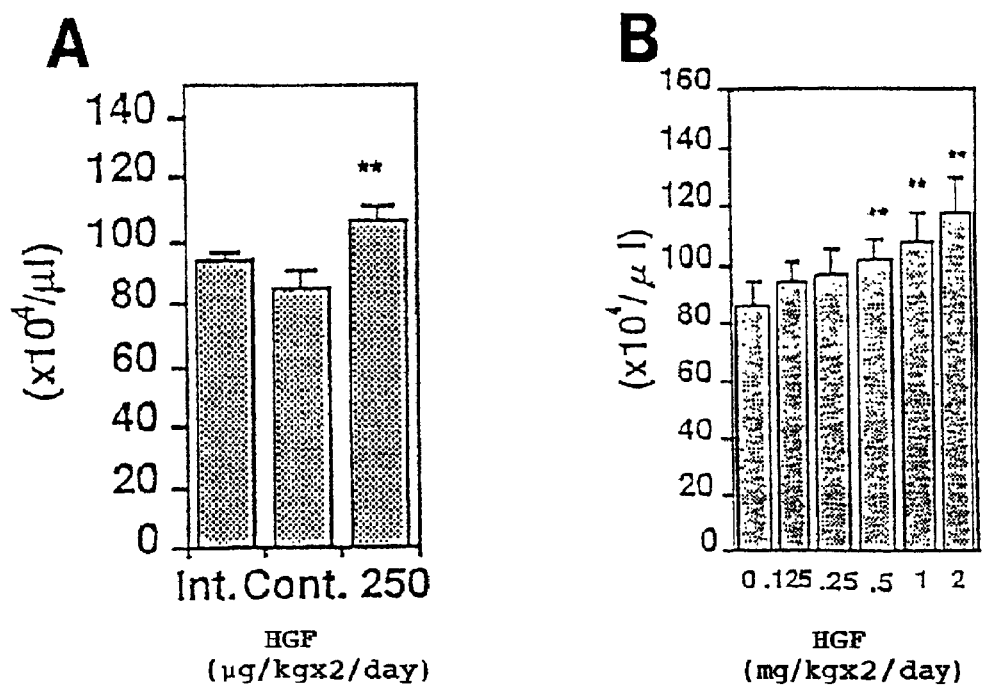
FIG. 13 is a graph showing increase of platelet counts by intravenous administration of HGF, in which A represents continuous intravenous administration of HGF (mean±SD, n=3, : p<0.01 to control), and B represents intravenous bolus administration of HGF (mean±SD, n=6, : p<0.01 to control).

Results are shown in FIG. 13. In the case of bolus administration, platelet counts were significantly increased at dose of 0.5 mg/kg×2/day or more. In continuous administration, platelet counts were significantly increased at dose of 0.25 mg/kg×2/day. Hence, by continuous administration, platelet counts were increased at a lower dose.

Preparation Example 1

A solution containing 1 mg of HGF, 1 g of mannitol, and 10 mg of polysorbate 80 in 100 ml of physiological saline was aseptically prepared, and 1 ml aliquot of the solution were poured into vials separately. They were lyophilized and sealed to obtain lyophilized preparations.

Preparation Example 2

A solution containing 1 mg of HGF and 100 mg of human serum albumin in 100 ml of 0.02M Phosphate buffer (containing 0.15M NaCl and 0.01% polysorbate 80; pH 7.4) was aseptically prepared, and 1 ml aliquot of the solution were poured into vials separately. They were lyophilized and sealed to obtain lyophilized preparations.

What is claimed is:

1. A method for treating renal failure, which comprises administering an effective amount of hepatocyte growth factor (HGF) by continuous intravenous administration to suppress blood urea nitrogen (BUN) and creatinine levels in a patient suffering from renal failure, thereby treating renal failure in said patient.

* * * * *